United States Patent [19]
Humphrey et al.

[11] Patent Number: 5,633,374
[45] Date of Patent: May 27, 1997

[54] PYRIMIDINE, CYANOGUANIDINES AS K-CHANNEL BLOCKERS

[75] Inventors: Stephen J. Humphrey; Kaushik D. Meisheri; James H. Ludens, all of Kalamazoo; Jackson B. Hester, Jr., Galesburg, all of Mich.

[73] Assignee: The Upjohn Company, Kalamazoo, Mich.

[21] Appl. No.: 553,308

[22] PCT Filed: Jul. 21, 1993

[86] PCT No.: PCT/US93/11332

§ 371 Date: Nov. 20, 1995

§ 102(e) Date: Nov. 20, 1995

[87] PCT Pub. No.: WO94/29280

PCT Pub. Date: Dec. 22, 1994

[51] Int. Cl.$^6$ .................. C07D 239/42; C07D 239/48
[52] U.S. Cl. .................. 544/322; 544/298; 544/319; 544/325; 544/330
[58] Field of Search .................. 514/256, 275; 544/298, 322, 325, 330, 319

[56] References Cited

U.S. PATENT DOCUMENTS 4,057,636  11/1977  Petersen et al. .................. 424/263

FOREIGN PATENT DOCUMENTS 0 503 627 A1  9/1992  European Pat. Off. .

OTHER PUBLICATIONS

HJ Petersen, J. Med. Chem., 21(8):773–781, 1978.
JK Smallwood, et al., J. Card. Pharm., 12:102–109, 1988.
DW Robertson, et al., Ann. Reports Med. Chem., 10:91–99, 1989.

Primary Examiner—Yogendra N. Gupta
Attorney, Agent, or Firm—Donald L. Corneglio

[57] ABSTRACT

Pyrimidine-cyanoguanidine compounds of Formula I and its pharmaceutically acceptable acid addition salts wherein $R_1$ is hydrogen or methyl;

$R_2$ is $C_1$–$C_6$ alkyl, $C_2$–$C_6$ alkenyl, $C_2$–$C_6$ alkynyl, $C_3$–$C_5$ cycloalkyl, $C_3$–$C_5$, hydroxy methyl, cycloalkyl methoxy-$C_1$–$C_5$ alkyl, or $R_1$ and $R_2$ are combined to form a $C_3$–$C_6$ carbocyclic ring;

$R_3$ and $R_4$ are each independently selected to be hydrogen, $C_1$–$C_4$ alkyl, F, Cl, Br, I or $CF_3$;

$R_5$ is hydrogen, F or Cl;

$R_6$ is hydrogen, —$NH_2$, —$NHCH_3$, —$NHC_2H_5$, —$NHCH(CH_3)_2$, —$N(CH_3)_2$, —$N(C_2H_5)_2$, $NH(CH_2)_m$—$OC_1$–$C_3$ alkyl (where m is 2 or 3), —NHC(O) $C_1$–$C_3$ alkyl, Cl or Br; and n is 0 or 1.

The compounds of Formula I are potassium channel blockers useful in the treatment of cardiovascular disorders such as congestive heart failure and hypertension and as a diuretic.

5 Claims, No Drawings

PYRIMIDINE, CYANOGUANIDINES AS K-CHANNEL BLOCKERS

BACKGROUND OF THE INVENTION

This application is a 371 of pct/81593/11332 filed Jul. 21, 1993.

The present invention is directed toward pyrimidine-cyanoguanidine compounds which are potassium channel blockers useful in the treatment of cardiovascular disorders such as congestive heart failure and hypertension. The pyrimidine-cyanoguanidine compounds of this invention, unlike other cyanoguanidines, block potassium channel conduction in vascular smooth muscle and ATP-sensitive potassium channels in apical membranes of Kidney.

It is known that $K^+$ channels are important for regulating potassium excretion by the kidney and it has been proposed that inhibition of ATP-sensitive $K^+$ channel conduction in apical cell membranes of the thick ascending limb of Henle's loop would reduce potassium recycling across the membrane and thus reduce sodium resorption via the $Na^+$-$2Cl^-$-$K^+$ co-transporter. It has also been proposed that inhibition of the ATP-sensitive $K^+$ channels of apical membranes in principal cells of the initial and cortical collecting tubule would reduce $K^+$ secretion, the primary source of urinary potassium. $K^+$ channel antagonist activities necessary to produce the observed eukalemic natriuresis have been documented in the rat kidney.

The subject compounds are effective blockers for the ATP-sensitive potassium channels of the thick ascending limb of Henle's loop and the principal cells of the initial and cortical collecting tubules of the kidney. This activity results in an enhanced urinary excretion of sodium and water without enhanced potassium excretion. This provides a useful diuresis which is not complicated by an undesirable reduction in plasma potassium levels or hypokalemia.

Thus, the subject series of cyanoguanidines, although very closely related to the $K^+$ channel agonist pinacidil and related compounds, are potent $K^+$ channel antagonists.

INFORMATION DISCLOSURE STATEMENT

U.S. Pat. No. 4,057,636 discloses pyridylguanidine compounds structurally similar to the subject compounds except that the subject compounds have a branched methylene linking group to a phenyl which can be optionally substituted. Surprisingly, the subject compounds are potassium channel blockers whereas the compounds of U.S. Pat. No. 4,057,636 are potassium channel openers.

Pinacidil, its pyridine N-oxide and related pyridylcyanoguanidines are a class of compounds structurally related to the subject invention. Articles disclosing these compounds are as follows: Smallwood, J. K., *J. Card. Pharm.*, 12: 102–9 (1988); and Peterson, H. J., *J. Med. Chem.*, 21(8): 773–81 (1978).

Other publications include, JP 166119, published Jan. 2, 1991, discloses cyanoguanidine derivatives have a branched alkyl group at the C-1 position but no phenyl group attached thereto. GB 055209, Dec. 20, 1974, Leo Pharmaceutical, discloses N-cyano-N'-pyridyl guanidine as hypotensives.

European Patent application 92104287.5 discloses compounds having a pyridine N-oxide and amine substitutions although not linked to a phenyl.

The state of the art on potassium channel mechanisms and pinacidil is discussed in *Annual Reports in Medicinal Chemistry*, Robertson D. W., et at., 24, Ch 10, 91–100 (1989).

SUMMARY OF THE INVENTION

In one aspect the present invention is a compound of Formula I and its pharmaceutically acceptable acid addition salts

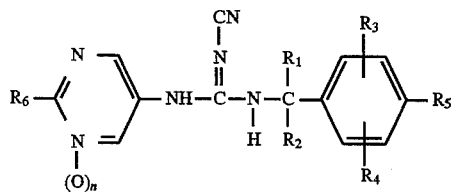

wherein $R_1$ is hydrogen or methyl;

$R_2$ is $C_1$–$C_6$ alkyl, $C_2$–$C_6$ alkenyl, $C_2$–$C_6$ alkynyl, $C_3$–$C_5$ cycloalkyl, $C_3$–$C_5$ cycloalkenyl, hydroxymethyl, methoxy-$C_1$–$C_5$ alkyl, or $R_1$ and $R_2$ are combined to form a $C_3$–$C_6$ carbocyclic ring;

$R_3$ and $R_4$ are each independently selected to be hydrogen, $C_1$–$C_4$ alkyl, F, Cl, Br, I or $CF_3$;

$R_5$ is hydrogen, F or Cl.

$R_6$ is hydrogen, —$NH_2$, —$NHCH_3$, —$NHC_2H_5$, —$NHCH(CH_3)_2$, —$N(CH_3)_2$, —$N(C_2H_5)_2$, —$NH(CH_2)_m$—$OC_1$—$C_3$alkyl (where m is 2 or 3), —$NHC(O)C_1$–$C_3$alkyl, Cl or Br,, and n is 0 or 1.

In another aspect, the subject invention is useful as a potassium channel blocker and can be used in the treatment of cardiovascular disorders such as congestive heart failure, hypertension and shock.

DETAILED DESCRIPTION OF THE INVENTION

The present invention is directed toward compounds of Formula I and its pharmaceutically acceptable acid addition salts, as structurally depicted above. The compounds of Formula I include both enantiomers as well as salts and tautomeric forms.

Preferably, at least one substituent is present on the benzylic carbon and when only one alkyl substituent is present the activity resides with the (R) enantiomer. Particularly preferred are compounds with small cycloalkyl, alkyl or $R_1R_2$ carbocyclic substituents on the benzylic carbon and with a 3-chloro or 3-fluoro substituent on the phenyl ring.

Pharmaceutically acceptable acid addition salts of the Formula I, may be chosen from the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethane-sulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate, and undecanoate.

The carbon content of various hydrocarbon-containing moieties is indicated by a prefix designating the minimum and maximum number of carbon atoms in the moiety, i.e., the prefix $C_i$–$C_j$ indicates a carbon atom's content of the integer "i" to the integer "j" carbon atoms, inclusive. For example, $C_1$–$C_3$ alkyl refers to alkyl of 1–3 carbon atoms, inclusive, or methyl, ethyl, propyl, and isopropyl, and isomeric forms thereof.

$C_3$–$C_5$ cycloalkyl is cyclopropane, cyclobutane, cyclopentane and isomeric forms thereof.

A "$C_3$–$C_6$ carbocyclic ring" means cyclopropyl, cyclobutyl, cyclopentyl, cyclohexyl, cyclobutenyl, cyclopentenyl or cyclohexenyl.

The compounds of Formula I will thus be useful for treating cardiovascular disorders such as congestive heart failure and forms of hypertension that can benefit from a reduction in plasma fluid volume. In addition, the compounds of this invention, by virtue of their potassium channel blocking activity, will be useful for preventing the undesirable increase in plasma renin activity that might be expected to result from a reduction of plasma fluid volume or from reductions in blood pressure by other co-administered antihypertensive agents. This activity will enhance the antihypertensive activities of both agents.

This invention thus contemplates the co-administration of compounds of Formula I with other antihypertensive agents such as the ACE inhibitors, the β-adrenergic blockers, the $\alpha_1$-adrenergic blockers, the $\alpha_2$-adrenergic agonists, calcium channel blockers, and other vasodilators such as the nitrates and hydralazine, etc. In addition, the compounds of Formula I are useful for their antiarrhythmic activity and their ability to antagonize overdoses of potassium channel agonists, to prevent excessive hair growth, to increase insulin release, to treat shock, to control reflex hyperemia and to reduce body weight.

The enantiomers of the compounds of Formula I in which $R_1$ and $R_2$ are different are considered to be important variations of this invention. When $R_1$ is hydrogen and $R_2$ is alkyl the preferred enantiomer has the (R) absolute configuration. Also important are the pharmacologically acceptable acid addition salts, the pharmaceutical preparations for oral, transdermal and parenteral administration and the novel chemical intermediates and processes for the preparation of the compounds of Formula I.

The compounds can be administered intravenously, intramuscularly, topically, transdermally such as by skin patches, buccally, suppositorally or orally to man or other animals. The compositions of the present invention can be presented for administration to humans and animals in unit dosage forms, such as tablets, capsules, pills, powders, granules, sterile parenteral solutions or suspensions, oral solutions or suspensions, oil in water and water in oil emulsions containing suitable quantities of the compound, suppositories and in fluid suspensions or solutions.

For oral administration either solid or fluid unit dosage forms can be prepared. For preparing solid compositions such as tables, the compound can be mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. Suspensions can be prepared with an aqueous vehicle with the aid of a suspending agent such as acacia, tragacanth, methylcellulose and the like.

For parenteral administration, fluid unit dosage forms can be prepared utilizing the compound and a sterile vehicle. In preparing solutions the compound can be dissolved in water for injection and filter sterilized before filling into a suitable vial or ampoule and sealing. Adjuvants such as a local anesthetic, preservative and buffering agents can be dissolved in the vehicle. The composition can be frozen after filling into a vial and the water removed under vacuum. The dry lyophilized powder can then be sealed in the vial and reconstituted prior to use.

As diuretic agents the compounds of Formula I can be used in unit dosages of 1 to 1000 mg in oral or injectable preparations.

CHEMISTRY

The subject compounds were prepared by the successive reaction of two amines with diphenyl cyanocarbonimidate (i). The first reaction was normally carried out with one

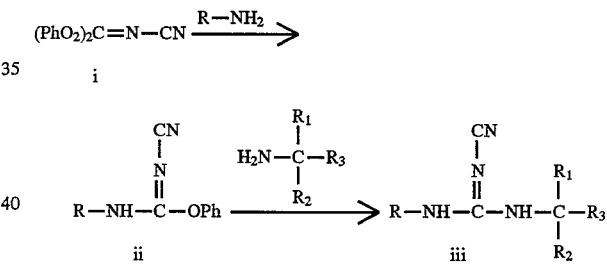

equivalent of the less reactive amine in $Et_2O$ or ethylene glycol dimethyl ether. In some cases, however, this procedure was unsuccessful and other solvents or conditions were required. For 5-pyrimidyl, where R in the above reaction scheme is 5-pyrimidyl, for example, it was necessary to warm the mixture of i and the amine to 50° C. in dimethoxyethane (DME). In the second step the second amine was usually allowed to react with ii in refluxing isopropanol or 1,4-dioxane. Other solvents such as dimethylformamide are also suitable for this reaction. This reaction required either two equivalents of the amine or one equivalent of the amine when an excess of N-methylmorpholine was employed.

TABLE I

Physical and Analytical Data for the Cyanoguanidines of Formula I

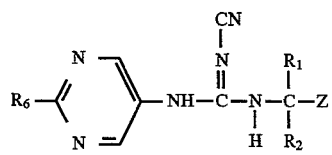

| Example # | $R_1$ | $R_2$ | Z | $R_6$ | mp, °C. | Recryst. Solvent |
|---|---|---|---|---|---|---|
| 1* | H | $CH_3$ | Ph | H | 203–204 | EtOAc |
| 2 | $-CH_2-CH_2-CH_2-$ | | Ph | $NH_2$ | 252–253(dec) | MeOH |

*(R) Enantiomer.

Compounds of the subject invention were tested for diuretic effect as well as potassium channel blocking activity.

The results for potassium channel blocking were obtained by using isolated rabbit mesenteric artery (RMA) procedures. Norepinephrine (5 µM) was used to contract the RMA rings twice, with an hour separating the two contractions. During this hour the tissues equilibrated in physiological salt solution at a resting tension of 1 gram. Upon the plateau of the second contraction 1 µM pinacidil was added to all tissues and the resulting relaxation time course was studied for thirty minutes. Pinacidil at this concentration has been shown to produce maximal $K^+$ channel dependent vasodilation in the system. By studying the ability of the test compounds to inhibit this pinacidil-induced relaxation, the degree of potassium antagonism could be determined. The compounds were applied to the tissues for one hour between the two contractions and the pinacidil-induced relaxation was studied in the continuing presence of the compounds. Thus, the total time of pretreatment with the test compound was 75 minutes before the addition of pinacidil. Only one tissue was used per concentration of each compound, and in the case of no relaxation, the tissues were shown to be capable of relaxation by known vasodilators. The compounds were tested at 5 µM. The inhibitory effect of a compound was measured as percent inhibition of pinacidil relaxation at 15 minutes in comparison with the control.

The diuretic activity was determined in female Harlan Sprague-Dawley rats weighing 200 to 230 grams that were fasted 15 hours overnight, and then were deprived of both food and water for an additional hour prior to dosing. Table II shows the measurement of net increase (above control) in urinary $Na^+$ excretion (µEq) for a 5 hour test period divided by the total of the three drag doses (mg/kg) administered IP in the diuretic screen. It approximates the area under the dose response curve. The vehicle was 20% dimethylacetamide (DMA; v/v) in a pH 7.4 phosphate buffer (0.58% $Na_2HPO_4$ and 0.13% $NaH_2PO_4 \cdot H_2O$). Sufficient drug was suspended in 1 to 2 ml of this vehicle to deliver doses of 1.0 to 30 mg/kg in a volume of 0.5 ml (2–4 rats/dose). At least 2 vehicle control rats, and, for most tests, 2 standard diuretic treated rats were included in each experiment. Standards used as comparators included the $K^+$ retaining diuretic amiloride and the $K^+$ wasting diuretics furosemide, hydrochlorothiazide and metolazone.

Following their IP doses, the rats' urinary bladders were gently compressed to eliminate all pretreatment urine, and two identically treated rats were placed in a stainless steel metabolism cage equipped with a graduated test tube to collect voided urine. At 2 and 5 hours post treatment, the rats' bladders were again compressed, the volume of urine excreted by the pair of rats was recorded, and aliquots of urine were retained for analysis of $Na^+$ and $K^+$ concentrations with a NOVA-13 selective ion analyzer. Following the 5 hour urine collection, the rats were returned to their stock cages, and at least 1 week of recovery was allowed between a maximum of 3 diuretic tests.

The electrolyte concentrations detected in these urine samples were manually multiplied by their respective volumes to determine total milliequivalent (mEq) excretion of $Na^+$ and $K^+$ per pair of rats, and the results obtained with multiple racks per drug treatment were averaged. Increases in urinary $Na^+$ excretion of 50% or more above the pooled control tests were regarded as reflecting activity.

Data for $K^+$ channel antagonist activity on rabbit mesenteric artery (RMA) and natriuretic efficacy after intraparenteral (IP) administration to rats are collected in Table II.

TABLE II

Natriuretic and Vascular Potassium Channel Antagonist Activities for the Compounds in Table I.

| Compound Example 77# | RMA $K^+$ Channel Antagonism % I at 5 µM[a] | 5 h Net Natriuretic Efficacy (µEq $Na^+$/mg/kg)[c] |
|---|---|---|
| Control* | $0.0 \pm 0.0$ (2)[b] | 0.0 |
| Pinacidil** | 0.0 (1) | $-60$[d] |
| 1 | $81.7 \pm 4.4$ (3) | 13.2 |
| 2 | 97 | 43 |

Notes for Table II
*Not a compound of the subject invention; R of Formula iii is 3-pyridyl, $R_1$ and $R_2$ are H and $R_3$ is $CH(Ph)_2$.
**Not a compound of the subject invention.
[a]This is a measure of a compound's ability to inhibit the relaxation of norepinephrine (5 µM) contracted rabbit mesenteric artery rings by pinacidil (1 µM). It is expressed as percent inhibition (mean ± sem) at an inhibitor concentration of 5 µM. Compounds with 65% or greater inhibition at 5 µM are considered to be active, with 20–65% inhibition moderately active and with less than 20% inhibition inactive.
[b]Number of mesenteric rings used for the determination.
[c]This represents the net increase (above control) in urinary $Na^+$ excretion (µEq) for the 5 hour test period divided by the total of the three drug doses (mg/kg) administered IP in the stage II diuretic screen in rats. It approximates the area under the dose response curve.
[d]Antidiuresis seen with 5 mg/kg oral dosage. Similar responses have been obtained with IP and IV administration.

Table II shows that the compounds of the invention have good potassium channel antagonist activity as well as natriuretic activity.

EXAMPLE 1

(R)-N''-Cyano-N-(5-pyrimidyl)-N'-(1-phenyl) ethylguanidine

A stirred mixture of diphenyl cyanocarbonimidate (1.05 g, 0.00442 mol), 5-amino-pyrimidine (0.42 g, 0.00442 mol) and $Et_2O$ (15 mL) was kept at ambient temperature for 4 days and at reflux for one day. There was little reaction. The solvent was evaporated and the residue was mixed with DME and warmed at 50°–55° for 2 days. The mixture was cooled, diluted with $Et_2O$ and filtered; the solid was washed with $Et_2O$ and dried to give 0.57 g of N'-Cyano-N-(5-pyrimidyl)-O-phenylisourea product.

A stirred mixture of N'-cyano-N-(5-pyrimidyl)-O-phenylisourea (0.5 g, 0.00209 mol), (R)-α-methylbenzylamine (1.0 mL) and DMF (4 mL) was kept, under nitrogen, at ambient temperature for 18 hours and concentrated in vacuo. The residue was allowed to crystallize from EtOAc-tert-butyl methyl ether. The solid was triturated with $Et_2O$ and tert-butyl methyl ether and crystallized from EtOAc to give product: NMR ($CDCl_3$) δ1.61 (d, 3H), 4.92 (m, 1H), 6.05 (broad s, 1H), 7.38 (m, 6H), 8.56 (s, 2H), 8.97 (s, 1H); IR (Nujol) 3262, 3109, 3054, 2174, 1600, 1570 $cm^{-1}$; MS m/z (relative intensity) 266 ($M^+$, 100), 251 (24.3), 161 (4.0), 146 (33.0), 120 (40.5), 105 (100).

EXAMPLE 2

N-(2-Amino-5-pyrimidyl)-N''-cyano-N'-(1-phenyl) cyclobutylguanidine

A stirred mixture of 2,5-diaminopyrimidine [Raiziss, G. W. and Freifelder, M., J. Am. Chem. Soc., 64:2340 (1942)] (0.65 g, 5.9 mmol) and ethylene glycol dimethyl ether (10 ml), under nitrogen, was treated during 2 minutes with diphenyl cyanocarbonimidate (1.41 g, 5.9 retool) and kept at ambient temperature (24° C.) for 20 hours. It was then diluted with $Et_2O$ and the resulting solid was collected by filtration, washed with $Et_2O$ and dried to give 1.40 g (93%) of product, N-(2-amino-5-pyrimidyl)-N'-cyano-O-phenylisourea: mp 257°–259° C., IR (Nujol) 2924, 2194, 1614, 1559 $cm^{-1}$; MS m/z (relative intensity) 254 ($M^+$, 40.6), 161 (42.2), 118 (25.2), 94 (100); NMR [($CD_3$)$_2$SO] δ6.83 (s, 2h), 7.30 (m, 3H), 7.44 (m, 2H), 8.31 (s, 2H), 10.45 (broad s, 1H).

A stirred mixture of N-(2-amino-5-pyrimidyl)-N'-cyano-O-phenylisourea (1.2 g, 4.72 mmol), 1-amino-1-phenylcyclobutane (0.70 g, 4.77 mmol), 4-methylmorpholine (1.3 ml, 11.8 mmol) and 1,4-dioxane (25 ml) was refluxed, under nitrogen, for 24 hours and kept at ambient temperature for 24 hours. The resulting precipitate was collected by filtration and crystallized from acetonitrile to give 0.70 g (48.3%) of the titled product, mp 251°–253° C. (dec). The analytical sample was recrystallized from methanol and had: mp 252°–253° C. (dec.); IR (Nujol) 3293, 2925, 2159, 1589, 1582, 1553 $cm^{-1}$; MS m/z (relative intensity) 307 ($M^+$, 33.7), 279 (37.3), 160 (25.3), 120 (100); NMR [($CD_3$)$_2$SO]δ1.75 (m, 1H), 1.90 (m, 1H), 2.45 (m, 4H), 6.78 (s, 2H), 7.22 (m, 1H), 7.39 (m,4H), 7.68 (s, 1H), 8.03 (s, 2H), 8.43 (s, 1H). Anal. Calc'd for $C_{16}H_{17}N_7$: C, 62.52; H, 5.58; N, 31.90. Found: C, 62.32; H, 5.45; N, 32.00.

We claim:

1. A compound of Formula I and its pharmaceutically acceptable acid addition salts

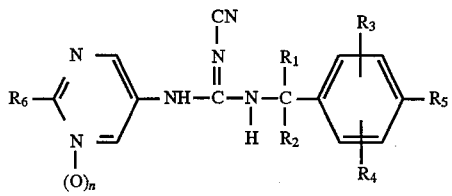

wherein $R_1$ is hydrogen or methyl;

$R_2$ is $C_1$–$C_6$ alkyl, $C_2$–$C_6$ alkenyl, $C_2$–$C_6$ alkynyl, $C_3$–$C_5$ cycloalkyl, $C_3$–$C_5$ cycloalkenyl, hydroxy methyl, methoxy-$C_1$–$C_5$ alkyl, or $R_1$ and $R_2$ are combined to form a $C_3$–$C_6$ carbocyclic ring;

$R_3$ and $R_4$ are each independently selected to be hydrogen, $C_1$–$C_4$ alkyl, F, Cl, Br, I or $CF_3$;

$R_5$ is hydrogen, F or Cl;

$R_6$ is hydrogen, —$NH_2$, —$NHCH_3$, —$NHC_2H_5$, —$NHCH(CH_3)_2$, —$N(CH_3)_2$, —$N(C_2H_5)_2$, $NH(CH_2)_m$—$OC_1$–$C_3$ alkyl, (where m is 2 or 3), —NHC(O) $C_1$–$C_3$ alkyil, Cl or Br, and n is 0 or 1.

2. The compound of claim 1 where $R_1$ and $R_2$ are joined to form cyclobutyl.

3. The compound of claim 1 where $R_1$ is hydrogen and $R_2$ is ethyl.

4. The compound of claim 1 where $R_6$ is $NH_2$, $NHCH_3$ or $NHC_2H_5$.

5. The compound of claim 1 which is a) (R)-N''-Cyano-N-(5-pyrimidyl)-N'-(1-phenyl) ethylguanidine;

b) N-(2-Amino-5-pyrimidyl)-N''-cyano-N'-(1-phenyl) cyclobutylguanidine.

* * * * *